(12) United States Patent
Bruni et al.

(10) Patent No.: US 11,850,105 B2
(45) Date of Patent: Dec. 26, 2023

(54) TILTING SEAT WITH LOWERED JOINT

(71) Applicants: Piero Giovanni Nicola Maria Bruni, Milan (IT); Giampiero Campanelli, Milan (IT); Marta Cavalli, Milan (IT)

(72) Inventors: Piero Giovanni Nicola Maria Bruni, Milan (IT); Giampiero Campanelli, Milan (IT); Marta Cavalli, Milan (IT)

(*) Notice: Subject to any disclaimer, the term of this patent is extended or adjusted under 35 U.S.C. 154(b) by 106 days.

(21) Appl. No.: 17/623,414

(22) PCT Filed: Jul. 20, 2020

(86) PCT No.: PCT/EP2020/070488
§ 371 (c)(1),
(2) Date: Dec. 28, 2021

(87) PCT Pub. No.: WO2021/018655
PCT Pub. Date: Feb. 4, 2021

(65) Prior Publication Data
US 2022/0346909 A1   Nov. 3, 2022

(30) Foreign Application Priority Data
Jul. 26, 2019 (IT) .......................... 102019000013056

(51) Int. Cl.
*A47C 9/00*   (2006.01)
*A61B 90/60*   (2016.01)
(Continued)

(52) U.S. Cl.
CPC ................ *A61B 90/60* (2016.02); *A47C 3/18* (2013.01); *A47C 7/029* (2018.08); *A47C 7/503* (2013.01); *A47C 7/006* (2013.01)

(58) Field of Classification Search
CPC ........... A47C 9/02; A47C 9/005; A47C 7/004; A47C 7/006; A47C 3/20; A47B 2200/0096
(Continued)

(56) References Cited

U.S. PATENT DOCUMENTS

| 135,924 A | * | 2/1873 | Lyon | ...................... A47C 9/005 248/397 |
| 3,029,106 A | | 4/1962 | McGuire | |

(Continued)

FOREIGN PATENT DOCUMENTS

| CN | 205988105 U | 3/2017 |
| DE | 19504838 A1 | 7/1995 |

(Continued)

OTHER PUBLICATIONS

International Search Report for international PCT Application No. PCT/EP2020/070488 filed on Jul. 20, 2020 on behalf of Bruni, Piero, Giovanni, Nicola, Maria, dated Sep. 1, 2020. 4 Pages.
(Continued)

Primary Examiner — Rodney B White
(74) Attorney, Agent, or Firm — Steinfl + Bruno LLP

(57) ABSTRACT

A tilting seat for operators in a controlled environment, particularly for surgeons and the like, comprising a saddle, a chest support, a forehead support and a leg support connected to a base standing on the ground, such that the saddle, the chest support, the forehead support and the leg support are integrally movable with rotation about a horizontal-axis joint placed below the saddle, keeping the space over the joint free from movable elements while in use, guaranteeing the substantial lack of contamination in such space.

20 Claims, 4 Drawing Sheets

Figure 1:
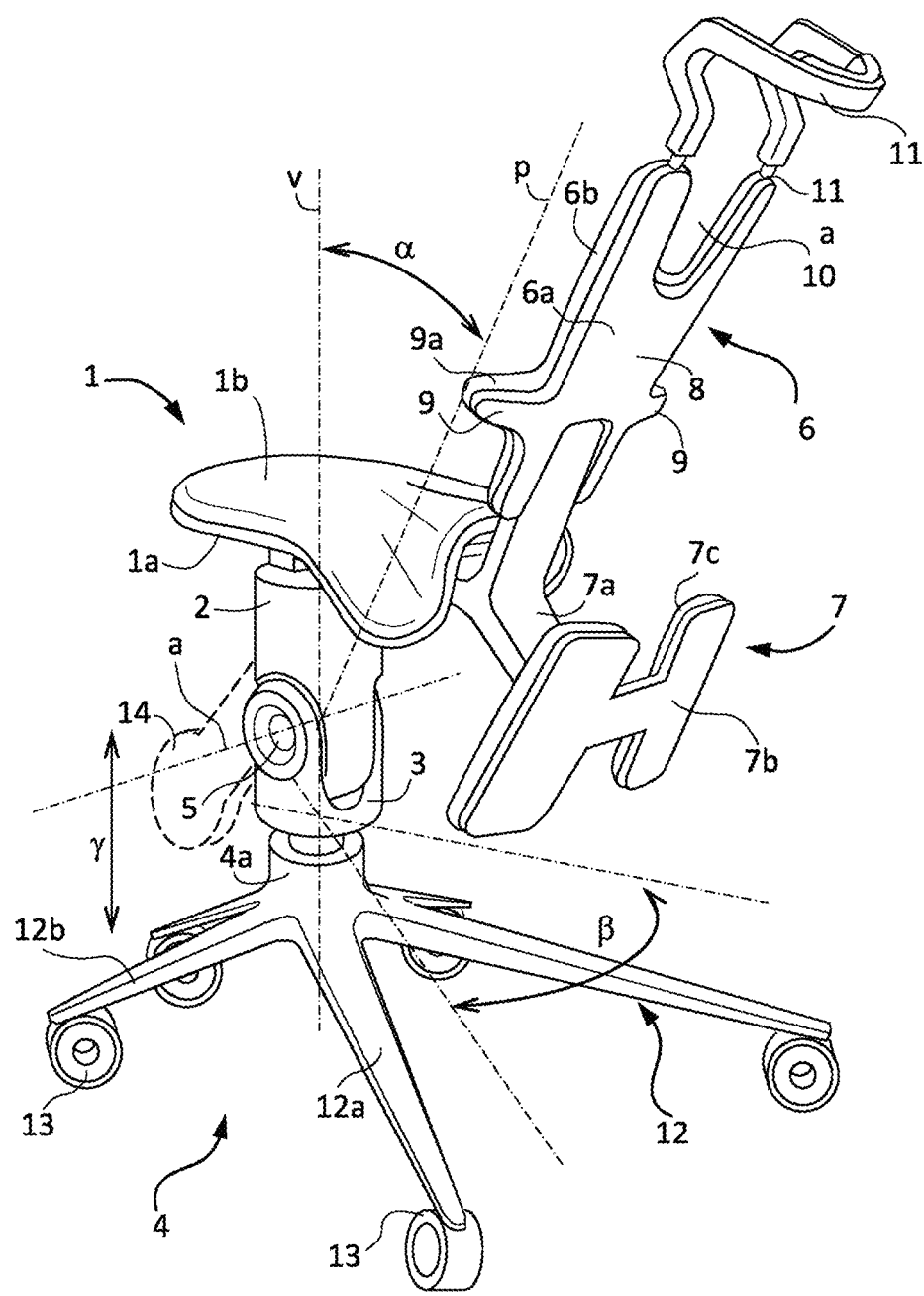

(51) Int. Cl.
*A47C 7/02* (2006.01)
*A47C 3/18* (2006.01)
*A47C 7/50* (2006.01)
*A47C 7/00* (2006.01)

(58) Field of Classification Search
USPC .......................... 297/423.11, 423.12, 195.11
See application file for complete search history.

(56) References Cited

U.S. PATENT DOCUMENTS

| | | | |
|---|---|---|---|
| 3,754,787 A | 8/1973 | Garber | |
| 4,510,633 A * | 4/1985 | Thorne | A61G 7/1094 |
| | | | 297/423.12 X |
| 4,607,882 A * | 8/1986 | Opsvik | A47C 9/002 |
| | | | 297/195.11 |
| 4,765,684 A * | 8/1988 | Kvalheim | A47C 13/00 |
| | | | 297/423.13 X |
| 4,832,407 A * | 5/1989 | Serber | A47C 9/005 |
| | | | 297/423.12 |
| 5,029,941 A | 7/1991 | Twisselmann | |
| 5,054,857 A * | 10/1991 | Kvalheim | A47C 13/00 |
| | | | 297/423.12 X |
| 5,261,723 A * | 11/1993 | Hosoe | A47C 9/005 |
| | | | 297/344.14 |
| 5,490,716 A | 2/1996 | Naughton | |
| D412,416 S * | 8/1999 | Ritch | D6/708.23 |
| 6,030,037 A * | 2/2000 | Ritch | A47C 7/004 |
| | | | 297/331 |
| 6,619,747 B2 * | 9/2003 | Ko | A47C 9/025 |
| | | | 297/423.12 |
| 6,769,736 B2 * | 8/2004 | Roleder | A47C 9/005 |
| | | | 297/195.11 |
| 7,090,303 B2 * | 8/2006 | Kropa | A47C 9/002 |
| | | | 297/423.11 |
| 7,198,329 B1 * | 4/2007 | Larson | A47C 3/22 |
| | | | 248/157 |
| D549,015 S * | 8/2007 | Petrick | D6/708.24 |
| 7,261,368 B1 * | 8/2007 | Clausnitzer | A47C 9/002 |
| | | | 297/423.12 X |
| 7,325,873 B2 * | 2/2008 | Stewart | A47C 3/04 |
| | | | 297/239 |
| D615,324 S * | 5/2010 | Yamamoto | D6/696.1 |
| 8,220,872 B2 * | 7/2012 | Hong | A47C 9/025 |
| | | | 297/344.17 |
| D665,191 S * | 8/2012 | Yamamoto | D6/656.15 |
| D669,282 S * | 10/2012 | Yamamoto | D6/691.6 |
| D693,152 S * | 11/2013 | Yamamoto | D6/656.15 |
| D702,840 S * | 4/2014 | Blomquist | D24/164 |
| D722,696 S * | 2/2015 | Blomquist | D24/164 |
| 9,084,486 B1 * | 7/2015 | Richardson | A47C 7/004 |
| 9,345,332 B2 * | 5/2016 | Kieryllo | A47C 7/506 |
| 9,451,831 B2 * | 9/2016 | Richardson | A47C 7/006 |
| 9,510,682 B2 * | 12/2016 | Hasegawa | A47C 3/18 |
| 9,833,076 B2 * | 12/2017 | Walker | A47C 9/025 |
| D827,139 S * | 8/2018 | Henderson | D24/160 |
| D830,747 S * | 10/2018 | Harvey | D6/707.22 |
| 10,178,915 B1 * | 1/2019 | Sternlight | A47G 9/1081 |
| 10,342,355 B2 * | 7/2019 | Derecktor | A47C 9/005 |
| 10,506,881 B2 * | 12/2019 | Richardson | A47C 7/543 |
| 10,517,404 B2 * | 12/2019 | Hopper | A47C 7/543 |
| 10,524,573 B2 * | 1/2020 | Richardson | A47C 3/00 |
| 10,617,220 B2 * | 4/2020 | Sternlight | A47C 21/026 |
| D888,966 S * | 6/2020 | Robert | D24/185 |
| 10,780,003 B2 * | 9/2020 | Beyer | A47C 7/024 |
| 10,869,557 B2 * | 12/2020 | Sternlight | A47C 21/026 |
| 10,918,213 B2 * | 2/2021 | Fryer | A47C 7/38 |
| D921,408 S * | 6/2021 | Bergsma | D6/708.17 |
| 11,051,906 B2 * | 7/2021 | Nardo | A61B 90/60 |
| D955,147 S * | 6/2022 | Hirshburg | D6/708.23 |
| 11,471,345 B2 * | 10/2022 | Beyer | A47C 9/025 |
| 11,503,917 B2 * | 11/2022 | Toscano | B60N 2/18 |
| 11,528,996 B2 * | 12/2022 | Pierce | B60N 3/002 |
| 2003/0151288 A1 * | 8/2003 | Deisig | A47C 9/005 |
| | | | 297/313 |
| 2007/0052275 A1 * | 3/2007 | Ghilzai | A47C 1/11 |
| | | | 297/423.12 |
| 2007/0108805 A1 * | 5/2007 | Manning | A47C 7/40 |
| | | | 297/383 |
| 2010/0066042 A1 * | 3/2010 | Damouzehtash | B25H 5/00 |
| | | | 280/32.5 |
| 2010/0295357 A1 * | 11/2010 | Koehler | A47C 9/005 |
| | | | 297/463.1 |
| 2011/0163577 A1 | 7/2011 | Anastasov | |
| 2014/0265496 A1 * | 9/2014 | Magelund | A61B 90/60 |
| | | | 297/313 |
| 2014/0306060 A1 * | 10/2014 | Schomacker | B64D 11/0601 |
| | | | 244/118.6 |
| 2015/0123432 A1 * | 5/2015 | Ray | A61B 90/60 |
| | | | 297/188.01 |
| 2018/0153638 A1 * | 6/2018 | Paixao Correia | A61B 90/60 |
| 2019/0307255 A1 * | 10/2019 | Derecktor | A47C 7/503 |
| 2020/0085198 A1 * | 3/2020 | Derecktor | A47C 4/00 |
| 2020/0237474 A1 * | 7/2020 | Muller | A61B 90/60 |
| 2022/0183918 A1 * | 6/2022 | Behrendt | A47C 7/383 |

FOREIGN PATENT DOCUMENTS

| | | |
|---|---|---|
| DE | 202012007543 U1 | 9/2012 |
| WO | 2008/085174 A1 | 7/2008 |
| WO | 2013/078569 A1 | 6/2013 |

OTHER PUBLICATIONS

Written Opinion for international PCT Application No. PCT/EP2020/070488 filed on Jul. 20, 2020 on behalf of Bruni, Piero, Giovanni, Nicola, Maria, dated Sep. 1, 2020. 8 Pages.

* cited by examiner

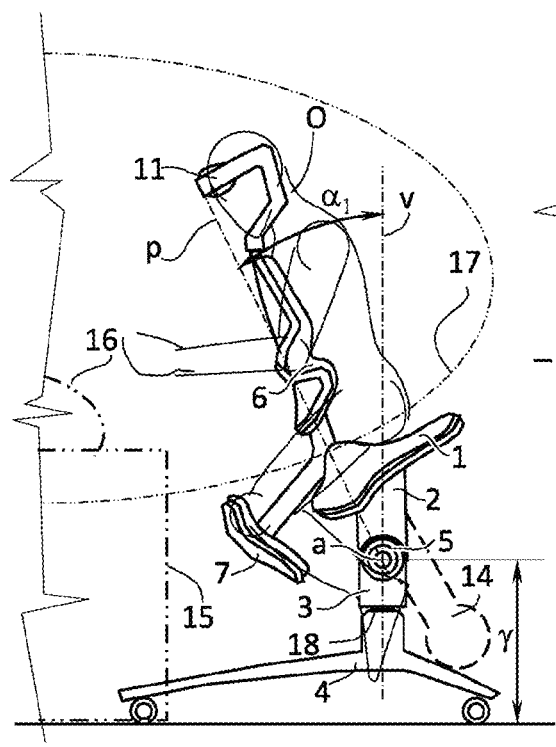
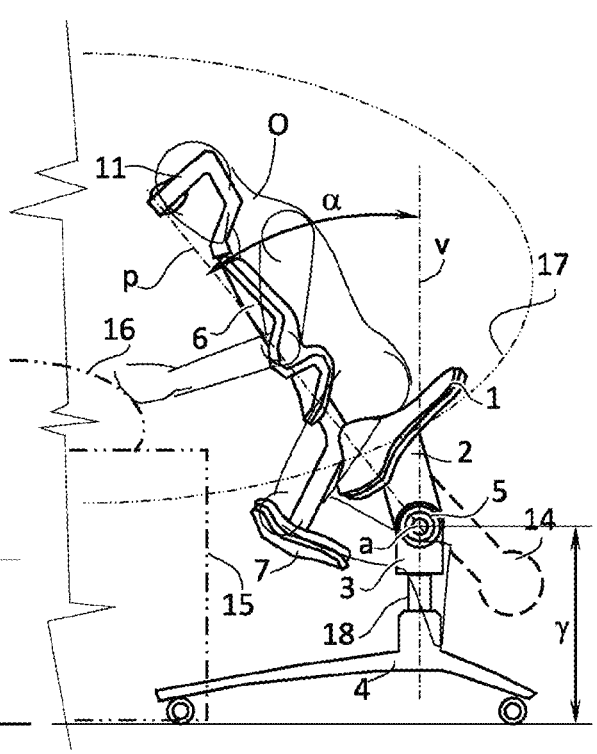
Fig. 4　　　　　　　Fig. 5
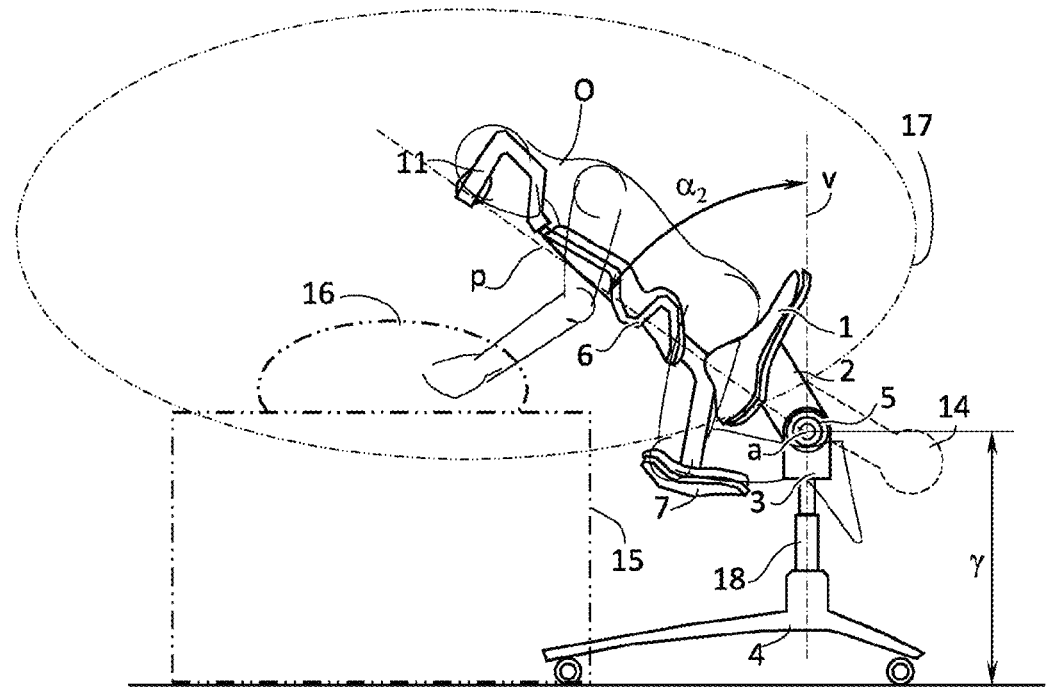
Fig. 6

TILTING SEAT WITH LOWERED JOINT

CROSS-REFERENCE TO RELATED APPLICATIONS

The present application is the U.S. National Stage of International Patent Application No. PCT/EP2020/070488 filed on Jul. 20, 2020 which, in turn, claims priority to Italian Application No. 102019000013056 filed on Jul. 26, 2019.

It is the object of the present invention a seat adapted to support and relieve from fatigue operators intended to work over an operating surface, such as operating tables, assembly and production lines, clean rooms and the like.

In particular, in a preferred embodiment the seat is useful to support and relieve from fatigue a surgeon during small/medium/big surgery carried out traditionally (namely, carried out in open surgery), as well as all the surgical procedures carried out by endoscopy/thoracoscopy/laparoscopy/robot-assisted and the like.

In many applications, and in particular in a surgical and medical environment, the operator is required to work in a facing position over a surface on which his work field is placed.

For example, a surgeon is required to work on his patient placed on an operating table. Usually, the surgeon operates while standing, in order to have an easy access and view over the operating field.

However, in case of long operations, for example of a few hours, the surgeon may experience fatigue, which can make it difficult for him to proceed with his activity.

Patent application US20110163577 discloses a seat system for surgeons which comprises a supporting structure, a seat adjustably connected to the support structure, a chest rest adjustably connected to the seat and at least an arm rest adjustably connected to the chest support.

U.S. Pat. No. 3,029,106 discloses an operative seat for surgeons having a seat which can be adjusted to support the surgeon at the desired height above the floor and having a body engaging member which may be adjusted to support the surgeon in a relaxed position relative to the patient during surgery.

Further surgeon seats are disclosed, for example, in patents U.S. Pat. Nos. 5,029,941; 5,490,716; DE19504838.

A problem observed in a surgical environment and the like is the need to guarantee maximum sterility. In particular, the equipment used in the operating room must be kept sterile after each surgery.

Within the scope of the present invention it was observed that in the operating room there is an area, typically below the plane of the operating table, which is in any case required be highly cleaned, but which does not necessarily need to be sterilized at the maximum level, and an area, over the plane of the operating table, where maximum sterility and lack of any kind of contamination are required.

It was thus observed that joints, mechanisms and the like, have rotation and sliding surfaces, for example threads, pins and the like, which define narrow corners and gaps, which are difficult to reach during cleaning operations and where dust and contaminants can accumulate over time; such components, furthermore, need to be lubricated, by means of oils, grease or other materials, which can in turn retain dust and contaminants, or represent a source of contamination. All this makes it difficult to ensure sterility and lack of contamination deriving from use, particularly when the seat is subject to a plurality of consecutive use cycles.

A further problem is that a seat for the operating room must be of simple structure so as to be cost-effective and ease its adoption by surgeons and the consequent hospital premises. Furthermore, a simple structure makes it more rapid and easier to carry out all the necessary cleaning and maintenance operations.

Furthermore, an operating room seat must not interfere with the surgeon's movements during the surgery step, it must coexist with existing apparatuses and operating tables, ensuring space ergonomics, offering a stable half-sitting position minimizing the distance of the surgeon form the operating table.

Furthermore, an operating room seat must comply with the criteria and norms of the operating rooms among which washability, impact and wear resistance.

Considering the above, it was found that by arranging the joint elements suitable for allowing the necessary operating mobility below the maximum sterility area, it is possible to offer a seat capable to support the operator and adapt to his operative needs, without compromising the sterility of the area requiring such sterility.

It is the object of the present invention a seat which comprises a saddle, a chest support, at least a leg support and a base, wherein the saddle, the chest support and the leg support are integrally movable in use with respect to the base, rotating about a horizontal axis joint placed below the saddle.

In one embodiment the seat comprises two leg supports, adapted to allow the knees to rest when desired during use.

Preferably the saddle comprises a forehead support that can be rigidly linkable to the chest support.

In one embodiment, the base comprises a vertical-axis body and several feet extended along a substantially radial direction from the body, preferably being angularly equally spaced.

Preferably, the base comprises two lockable wheels.

The integral horizontal rotation joint of the assembly consisting in the saddle, the chest support and the leg support comprises an elastic contrast element, yielding in a controlled way under the weight of the operator, adapted to allow the autonomous return of the assembly as the load diminishes.

The saddle, the chest support and the leg support are integrally movable with rotation about a vertical-axis rotatable support.

The base comprises at least four feet extended along a substantially radial direction, at least two of which having a radial extension greater than the others.

In such case, the vertical axis rotatable support of the assembly consisting in the saddle, the chest support and the leg support comprises abutments limiting rotation at a width equal or lower than 90°.

In one embodiment, the tilt junction in use of the assembly consisting in the saddle, the chest support and the leg support comprises an abutment limiting the tilt at an angle having width equal or lower than 50° between a laying axis, substantially parallel to the axis of the bust of the operator who is sitting on the seat laying the bust against the chest support and the vertical axis.

According to one embodiment, the saddle comprises a counterweight that is integral with the saddle.

In such case, the base comprises a vertical axis body and several feet extended along a substantially radial direction, having substantially equal length.

According to one embodiment, the saddle comprises at least a sterile cloth covering at least an element among saddle, chest support and leg support.

At least one of saddle, chest support and leg support can be previously adjusted into position, that cannot be modified while in use.

Preferably the seat is structured to accommodate a surgeon operating above an operating table.

Figure 2:
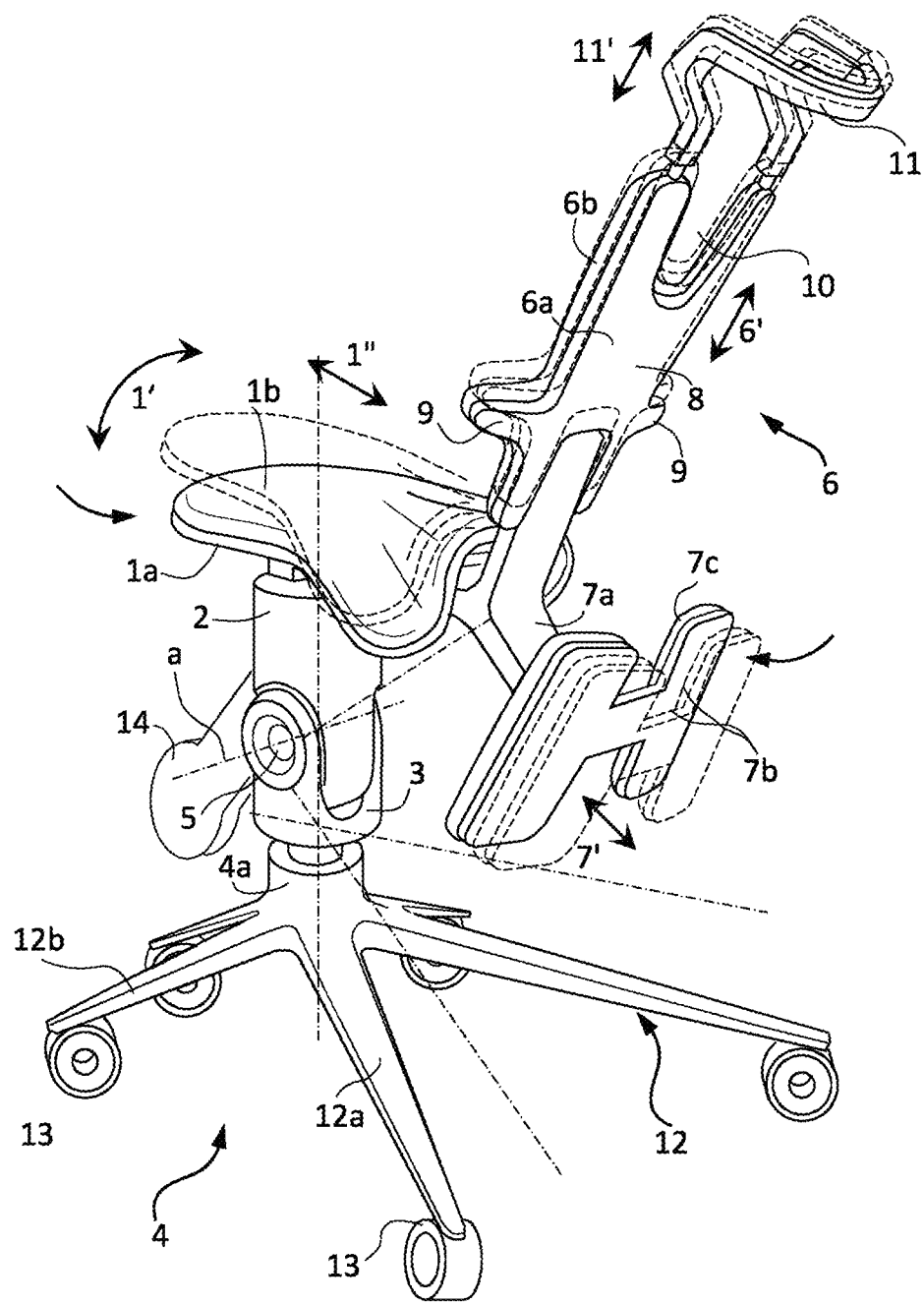
Figure 3:
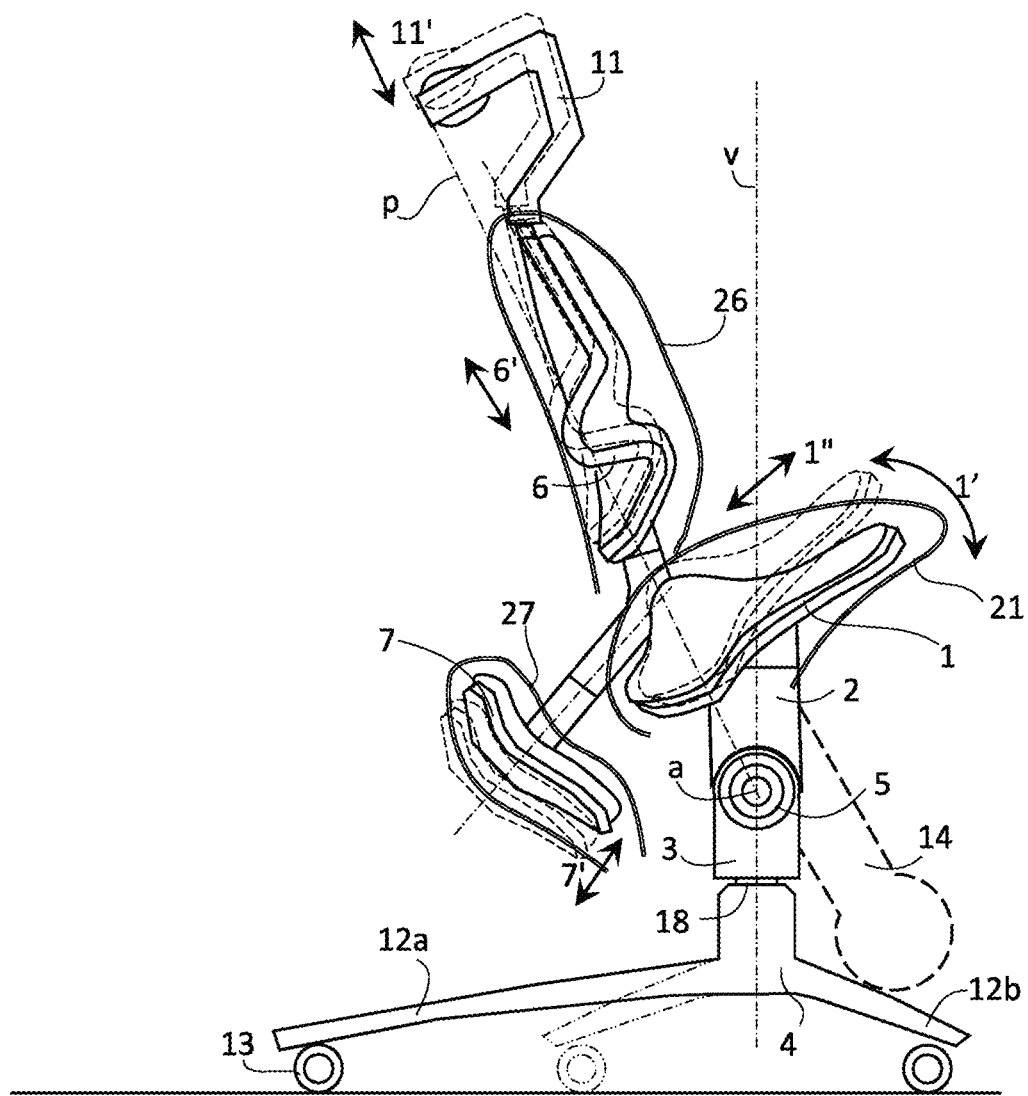

More details will be identified from the following description of one embodiment, with reference to the enclosed figures, wherein it is shown:

in FIG. 1 a perspective view of the seat, with the movements possible while in use being indicated;

in FIG. 2 a perspective view of the seat, with possible adjustment areas being indicated;

in FIG. 3 a schematic view of the seat in front of the operating table;

in FIG. 4 a schematic view of the seat in front of the operating table, with an operator in a first position;

in FIG. 5 a schematic view of the seat in front of the operating table, with an operator in a second position;

in FIG. 6 a schematic view of the seat in front of the operating table, with an operator in a third position.

As shown by the figures, the seat comprises an ergonomically-shaped saddle 1, linked to a support 2, in turn linked to the yoke 3 of a base 4, by means of a joint 5 having a horizontal axis "a".

The saddle 1 is in turn linked to the chest support 6 and to a pair of leg supports 7.

The joint 5, provided with a calibrated spring mechanism or similar mechanical or motorized device, allows the saddle 1, and other elements linked thereto, hereinafter described, to rotate on the vertical plane, about the "a" axis, tilting forward and downward. For exemplary purposes, the rotation about the "a" axis can allow the assembly consisting of the saddle and the other elements integrally linked thereto to change inclination a of its own laying axis "p", substantially parallel to the axis of the bust of the operator O who is sitting on the seat laying the bust against the chest support 6, with respect to the vertical axis "v" between a minimum angle $\alpha_1$ of about 10-15° and a maximum angle $\alpha_2$ preferably of about 45-50°.

The chest support 6 preferably comprises a central portion 8 and two elbow rest supports 9. At the upper end of the chest support 6 an opening 10 is preferably present, that is adapted to enable the operator sitting on the seat to have complete view and head mobility. In the upper part of the chest support 6 there are also housings 11a for inserting a forehead support 11.

The forehead support 11 may comprise one or more accessories such as the frontal light, an analog/digital visor, a protection screen, earphones, microphone and similar equipment which is useful for the operator.

Preferably, the forehead support 11 is made of flexible material, for example polymeric, such to comfortably accommodate the operator's forehead and allow the lateral movements required in use, while maintaining at the same time a support function.

The saddle 1 preferably comprises a base 1a, linked to the support 2 and a deformable coating 1b, adapted to provide the necessary comfort.

The chest support 6 comprises in turn a rigid frame 6a and a deformable coating 6b.

The elbow rests 9 are in turn preferably coated with lateral coatings 9a, which can be lateral portions of the deformable coating 6b of the chest support 6, or, in alternative, free-standing elements.

The leg supports 7 are constrained to a rod 7a, which extends from the base 1a of the saddle 1, and comprise a frame 7b, integral with the rod 7a, and a deformable coating 7c, adapted to enable comfortable and stable support for the operator's knees as required.

Preferably, the rod 7a is rigidly linked to the base 1a of the saddle 1, and can extend in a longitudinal direction, for example in a telescopic manner, to allow prior adjustment based on the user's anatomy and preferences.

The base 4 comprises a body 4a, which the yoke 3, and five feet 12 provided with wheels 13, conveniently equipped with a relative locking device, for example pedal-controllable (not shown), are linked.

The yoke 3 is linked to the body 4a according to a telescopically rotatable and extensible motion, for example by means of a calibrated vertical piston, a gas spring or similar, which enables to adjust the height of the whole seat, for example by means of a control manual lever, namely another mechanical or motorised device, and the rightwise and leftwise rotation on the horizontal plane.

In use, the user can at any time rotate the saddle 1 by leveraging on his legs, which thus will have to be disengaged from one or both leg supports 7.

Preferably the base 4 comprises two longer front feet 12a, and three shorter back feet 12b, extended along substantially radial directions from the body 4a. Preferably, the horizontal rotation angle β of the seat 1 is limited to an angle of about 90°, at the longer front feet 12a. Mechanical stops or the like ensure limitation of the stroke beyond 90°. This enables to avoid the risk of overturning, maintaining the barycentre of the seat assembly and operator within the base.

The seat can comprise a saddle 1 counterweight 14 (fixed or adjustable in extension), which counterweights the forward displacement of the operator in case of inclination of the seat. In such case, it is possible to make all of the base 4 feet 12 of equal length, or in any case limit the higher length of front feet 12a with respect to the others, for instance in case there are limitations to the length of the front feet 12s.

Adjustments of the height of the chest support 6, extension of the leg supports 7, forehead support 11, saddle position and inclination 1, represented in FIGS. 2 and 3 by a dotted line and respectively indicated with references 6', 7', 11', 1', 1" and possible further adjustments, are made in a separate environment, outside the operating room, to adapt to the surgeon anatomy, and are no longer activated in use.

Thereby the respective adjustment and fixing devices stay locked and are no longer exposed to contamination or cause contamination when the seat is taken to the operating room.

In use, as shown in FIGS. 4, 5, 6, the seat is arranged in front of an operating table 15, on which a patient 16 is placed (schematically represented with dotted lines).

Preferably, in such step, as shown in FIG. 3, the saddle 1, the chest support 6, the leg support 7 and other possible elements can be covered with specific disposable or multiple-use sterile cloths 21, 26, 27, in compliance with the applied standards.

Once adjusted the support heights (in a non-sterile pre-operation step), such to be suitable for the user body-type, the seat can be entered into the operating room, possibly covered with sterile cloths, so as to make it possible to use it in the operating room in full compliance with the operating field sterility requirements.

In the operating room, based on his needs, when the user intentionally moves his weight from the ischium region to the pubic-perineal one exerting at the same time pressure on the saddle and on the chest support, and optionally also on the forehead support, to obtain a half-lying position, the entire assembly rotates integrally about the axis "a" of the joint 5, with a movement controlled by an elastic abutment mechanism, for example a calibrated spring or the like. Subsequently the user can automatically return to the original neutral position, once his own barycentre has moved back again to return to the initial ischium support.

As shown in FIGS. 4, 5, 6 the whole movement extension is provided only by the joint 5 which is arranged outside the zone 17 wherein maximum sterility must be maintained.

Below the joint 5, a vertical calibrated piston mechanism 18 or the like, linking the yoke 3 to the body 4a allows both rotating the assembly consisting of the saddle 1, the chest support 6 and the leg support 7 on the horizontal plane, and adjusting the height of the assembly, according to the arrow y; this component 18 is also arranged outside the zone 17 of maximum sterility.

The forehead and the chest supports (the latter shaped to ensure the utmost adherence with the meso sternal and epigastric region) tilt forward jointly with the saddle, tilting forward as well, every time the surgeon mechanically pushed with the chest or the forehead towards such direction, while the leg supports (which the operator can decide to use or not at any moment) move always jointly downward and backward, enabling the surgeon to assume a forward tilted position to an angle $\alpha_2$ between the vertical axis and the laying axis "p" of about 45-50°, that is half-lying. On both sides of the chest support, specific profiles for an optional and discreet support of elbows and forearms are present, that are included in the area made sterile by respective coatings (disposable/multiple-use standard ones or dedicated disposable ones), particularly useful when the forward stroke of the chest and forehead are limited.

The surgeon will now be able to benefit from a dynamic, extremely light and compact seat which will enable him to carry out any type of operation discharging forces and body weight not only on the ischium and perineal region, but also on the forehead, chest and legs, by projecting on the operating field from above assuming with respect to the patient a comfortable half-lying position that relieves fatigue from the muscles and body joints and reduces tremors due to fatigue and nervous stress by correcting the posture.

Keeping his feet on the ground, the surgeon may decide to move the seat in any direction before locking wheels. Once the seat is locked, the following movements are still possible:

raising/lowering the joint 5 (which all the supports are linked to) leaning forward as desired without ever overbalancing, even assuming a half-lying position, which is obtained using all the supports and reaching the maximum permitted angle by pushing forward his own weight;

rotating all the supports of about 90° on a horizontal plane (for example keeping at least a foot on the ground during use);

tilting the head rightwise and leftwise, both taking advantage of the flexibility of the plastic materials with which the two vertical supports of the forehead-stand are made, but also rotating the head from one side or the other within the wide forehead support, leaving the operator free to perform slight twists with the bust, without ever losing adherence with the chest support;

free movements of the upper and lower limbs.

Despite the previous invention is mainly directed to the use of the seat as an aid for the surgeon in the operating room, the seat according to the present invention can also be used in other situations wherein there are similar mobility and cleaning needs, such as for example electronic component assembly lines, clean rooms, synthesis or analysis laboratories and the like, wherein the area where the operator works must be kept particularly clean and free from contaminants, while offering the operator a seat position providing him with the best and most comfortable working conditions.

The invention claimed is:

1. A surgical seat comprising:
   a saddle,
   a chest support,
   at least one leg support and
   a base,
   wherein the saddle, the chest support and the at least one leg support are connected to the base by a yoke and a vertical piston mechanism, the yoke comprising a horizontal-axis joint placed below the saddle, and
   the saddle, the chest support and the at least one leg support are configured to be integrally movable with respect to the base when an operator is sitting on the surgical seat, with movements comprising:
   i) integral rotation of the saddle, the chest support and the at least one leg support about the horizontal-axis joint through body pressure of the operator on the saddle and the chest support, and
   ii) vertical extension of the vertical piston mechanism.

2. The surgical seat according to claim 1, wherein the at least one leg support comprises two leg supports.

3. The surgical seat according to claim 1, further comprising a forehead support rigidly linkable to the chest support.

4. The surgical seat according to claim 1, wherein the base comprises a vertical-axis body and feet extending from the body along substantially radial directions.

5. The surgical seat according to claim 4, wherein the feet are at least four feet, at least two feet of said at least four feet having greater radial extension than other feet of said at least four feet.

6. The surgical seat according to claim 4, wherein the feet are substantially angularly equally spaced.

7. The surgical seat according to claim 1, wherein the base comprises lockable wheels.

8. The surgical seat according to claim 1, wherein the horizontal-axis joint is configured to elastically yield in a controlled way under weight of an operator of the surgical seat.

9. The surgical seat according to claim 1, wherein the saddle, the chest support and the at least one leg support are further integrally movable with further rotation about a vertical-axis rotatable support housed in a body of the base.

10. The surgical seat according to claim 9, wherein the vertical-axis rotatable support is limited in rotation on a horizontal plane to an angle equal to or lower than 90°.

11. The surgical seat according to claim 1, wherein the rotation about the horizontal-axis joint is limited to an angle equal to or lower than 50°.

12. The surgical seat according to claim 11, wherein the base comprises a vertical-axis body and feet having substantially equal length and extending from the body along substantially radial directions.

13. The surgical seat according to claim 11, wherein the angle is between a laying axis, substantially parallel to an axis of a bust of an operator sitting on the surgical seat and laying the bust against the chest support and a vertical axis of the surgical seat.

14. The surgical seat according to claim 1, the surgical seat further comprising a counterweight integral with the saddle.

15. The surgical seat according to claim 1, further comprising at least one sterile cloth covering at least one of said saddle, said chest support or said at least one leg support.

16. The surgical seat according to claim 1, wherein at least one of said saddle, said chest support or said at least one leg support is adjustable into an operative position prior to use, said operative position being unmodifiable in use.

17. The surgical seat of claim 1, wherein the vertical piston mechanism is a vertical calibrated piston mechanism.

18. The surgical seat of claim 1, wherein the surgical seat is configured to enable the operator sitting on the surgical seat to operate within a sterility zone, and the horizontal-axis joint is located below the saddle and outside the sterility zone during the saddle- and chest-activated integral rotation of the saddle, the chest support and the at least one leg support.

19. A seat comprising:
a saddle,
a horizontal-axis joint placed below the saddle,
a chest support,
at least one leg support and
a base,
wherein the saddle, the chest support and the at least one leg support are configured to be integrally movable with respect to the base when an operator is sitting on the seat, with rotation about the horizontal-axis joint and are further integrally movable with further rotation about a vertical-axis rotatable support housed in a body of the base, and
the vertical-axis rotatable support is limited in rotation on a horizontal plane to an angle equal to or lower than 90°.

20. A seat comprising:
a saddle,
a horizontal-axis joint placed below the saddle,
a chest support,
at least one leg support,
a base, and
a counterweight integral with the saddle,
wherein the saddle, the chest support and the at least one leg support are configured to be integrally movable with respect to the base when an operator is sitting on the seat, with rotation about the horizontal-axis joint.

* * * * *